United States Patent [19]

Kollonitsch

[11] 4,004,996
[45] Jan. 25, 1977

[54] FLUORINATION OF ORGANIC COMPOUNDS
[75] Inventor: Janos Kollonitsch, Westfield, N.J.
[73] Assignee: Merck & Co., Inc., Rahway, N.J.
[22] Filed: Dec. 23, 1974
[21] Appl. No.: 535,878
[52] U.S. Cl. .................... 204/158 HA; 260/78 SC; 260/96 HA; 260/534 R; 260/534 C; 260/583 G; 260/583 GG; 260/584 R; 526/14; 526/17; 526/42; 526/270; 526/317; 526/343
[51] Int. Cl.² ................. C07C 87/22; C07C 91/06; C07C 101/10; B01J 1/10
[58] Field of Search ........ 204/158 HA; 260/534 R, 260/534 C, 583 G, 583 GG, 584 R

[56]  References Cited
UNITED STATES PATENTS
3,413,326  11/1968  Schmid ..................... 260/534 R X
3,839,170  10/1974  Kollonitsch ................ 260/534 C X OTHER PUBLICATIONS
Mercer et al., J. Phys. Chem., 63 (1959), 1468–1470.
Coon et al., J. Org. Chem. 33 (1968), 1387–1391.
Tanner, Chimia, 22 (1968), 176–184.

Primary Examiner—Richard L. Raymond
Attorney, Agent, or Firm—William H. Nicholson; Hesna J. Pfeiffer; Julian S. Levitt

[57]  ABSTRACT

Organic amines, amino acids, polyamides and vinyl-polymers are fluorinated by the action of fluorine in liquid hydrogen fluoride optionally containing boron trifluoride or antimony pentafluoride at about −80° to 15° C. and optionally under irradiation with light.

6 Claims, No Drawings

FLUORINATION OF ORGANIC COMPOUNDS

This invention is concerned with the substitutive C-fluorination of organic compounds with fluorine in the liquid or solid phase. In particular, it is concerned with the C-fluorination of organic amines, amino acids, polyamides and vinyl polymers dissolved in or suspended in anhydrous liquid hydrogen fluoride or mixtures of liquid hydrogen fluoride and boron trifluoride or liquid hydrogen fluoride and antimony pentafluoride with fluorine, optionally under irradiation with light.

More particularly, it is concerned with the fluorination of amino acids, especially D-alanine or its 2-deutero analog with fluorine in hydrogen fluoride, a mixture of hydrogen fluoride and boron trifluoride or a mixture of hydrogen fluoride and antimony pentafluoride, optionally under irradiation with light.

Still more particularly, it is concerned with the C-fluorination of D-alanine and its 2-deutero analog in liquid hydrogen fluoride/boron trifluoride mixtures under irradiation with light.

Prior to this invention the scope and utility of known methods for substitutive fluorination of organic compounds in the sense of the equation:

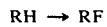

RH → RF were very limited. The most important methods available for the above type of transformation were (1) electrolytic fluorination in liquid hydrogen fluoride, (2) reaction with high valency oxidative metallic fluorides such as cobalt trifluoride, (3) reaction with perchloryl fluoride, (4) fluorination with fluoroxyperfluoroalkanes, and (5) reaction with fluorine.

The main limitations with methods (1) and (2) are that they usually result in mixtures of polyfluorinated compounds even in the case of substrates with simple structures. With more complex substrates, extensive degradation and carbon skeletal rearrangements often occur, thus severly limiting the yield and predictability of any individual product. In contrast, method (3), employing perchloryl fluoride, allows more selective fluorination, and does not generally cause degradation of the substrate, but is only effective with especially reactive substrates such as activated methylene groups.

Method (4), fluorination with fluoroxyperfluoroalkanes, such as fluoroxytrifluoromethane when conducted in the cold in the presence of U.V. irradiation, is a useful fluorination procedure but suffers the impediment of employing a rather expensive fluorinating agent.

Reaction with elemental fluoride, Method (5), as known in the art is of extremely limited utility because of the great reactivity of fluorine, fluorination usually proceeding spontaneously with explosive rapidity resulting in uncontrolled polyfluorination and degradation of the substrate.

There are examples of more controlled fluorination with fluorine in the prior art. For example, Mercer et al., *J. Phys. Chem.*, 63, 1468 (1959) described the gas phase fluorination of hydrogen-methane mixtures to give mainly $CH_3F$ and $CH_2F_2$ and some $CHF_3$ and $CF_4$, the rate of which was accelerated by a factor of about 2.5 by irradiation with a medium pressure mercury lamp. Coon et al. in *J. Org. Chem.*, 33, 1387 (1968) described the fluorination in hydrogen fluoride of nonbasic polynitroanilines to give N,N-difluoroamines and of basic anilines which resulted in decomposition of the starting materials. Tanner, in *Chimia* 22, 176–184 (1968) describes fluorination experiments on polyethylene. The tests were conducted on solid sheets of polyethylene and for any degree of success required pure fluorine as opposed to fluorine diluted with nitrogen, a high pressure ultraviolet light, and a high temperature.

Surprisingly, it has now been found that the limited usefulness of fluorine as a fluorinating agent can be greatly extended by conducting the fluorination reaction in anhydrous liquid hydrogen fluoride or mixtures of it with boron trifluoride or antimony pentafluoride.

The novel process of this invention comprises dissolving or suspending an amine, amino acid, polyamide, or a vinyl polymer to be fluorinated in liquid hydrogen fluoride or a mixture of liquid hydrogen fluoride and boron trifluoride or antimony pentafluoride, preferably the former, and bubbling fluorine through the solution or suspension for a time sufficient to produce the desired extent of fluorination.

The amount of boron trifluoride relative to that of hydrogen fluoride can be from zero to the saturation point. Similarly, antimony pentafluoride concentrations from zero to about 50% (w/w) preferably from 0–10% (w/w) are useful.

Any temperature between about −80° and 15° C. is satisfactory, but it is most convenient to conduct the reaction at about −78° C., the temperature of a dry-ice-/acetone bath.

Pure fluorine may be employed as reagent in this novel fluorination but because of its extremely hazardous properties including its great reactivity, it is preferred to use a mixture of fluorine with a rare gas such as helium neon, argon or the like, or nitrogen up to about 80% fluorine by volume, preferably mixtures containing from 1–20% fluorine by volume.

The amount of fluorine required depends on the degree of fluorination required and to some extent on the nature of the substrate, but usually a mole of fluorine or slight excess is sufficient for monofluorination.

While the fluorine is being delivered, the reaction mixture should be stirred or otherwise agitated. Fluorination under these conditions is sufficiently controlled to require, in some cases, irradiation with light from a medium pressure mercury lamp to promote the reaction in order that satisfactory reaction rates are realized. Reaction times of 1 to about 20 hours may be required, but are usually in the range of 2–6 hours.

A suitable reaction vessel is one machined from a Kel-F rod equipped with an ultraviolet-transparent window.

A convenient source of light radiation is a Hanovia mercury-xenon arc lamp No. 9778-1, run by a 1000 W. power supply, with the lamp mounted in a Schoeffel LH 15 1-N Projector equipped with a quartz condensor lens and a heat filter (water.)

The novel process of this invention provides a convenient route to a variety of C-fluoro amines and their acid addition salts useful as wetting agents, fluorinated amino acids and their salts useful as antibacterials and polyamide monomers, polyamides and vinyl polymers with improved properties. Of particular utility are 3-fluoro-D-alanine and 3-fluoro-2-deutero-D-alanine. These compounds are known antibacterial agents.

The acid addition salts encompassed by this invention are those prepared from the common mineral acids such as hydrofluoric, hydrochloric, hydrobromic, sulfuric, or the like.

The following examples are illustrative only and not intended to limit the scope of this invention to the particular substrates and conditions used therein.

EXAMPLE 1

3-Fluoro-D-Alanine from D-Alanine

D-Alanine (0.377g.) was dissolved in 30 ml. of liquid hydrogen fluoride at −78° C. Into this solution boron trifluoride gas was bubbled at −78° C. by careful evaporation of 5 ml. of liquid boron trifluoride. A fluorine/-helium mixture (2% fluorine by volume) was passed into the above solution at −78° C. for 2 hours while it was illuminated by a U.V. light source (about 5.2 milliatoms of fluorine). The reactor was allowed to warm to room temperature and the solvent was removed by bubbling nitrogen through the mixture. Analysis by Spinco automatic amino acid analyzer showed the presence of 3-fluoro-D-alanine together with some starting material. The product was separated by column chromatography on 200 ml. of Dowex 50×8 (200–400 mesh) cation exchange resin in the H+ form, by elution with 1 liter of water, 1.5 liters of 0.1 N hydrochloric acid, and then 1.2 liters of 0.3 N hydrochloric acid collecting the effluent in 15 ml. fractions. The 3-fluoro-D-alanine product was located by its color test with ninhydrin reagent in Tubes No. 50–61 obtained with the 0.3 N hydrochloric acid. Evaporation in vacuo of these fractions gave 3-fluoro-D-alanine hydrochloride which was recrystallized from a water-pyridine-isopropanol mixture and dried in vacuo; melting point 167°–168° C. (dec.)

$[\alpha]_D$ −9.1 ± 1° (c 3, 1 molar aqueous HCl).

EXAMPLE 2

2-Deutero-3-Fluoro-D-Alanine from 2-Deutero-D-Alanine

2-Deutero-D-alanine was fluorinated by exactly the same process as described in Example 1 and the product had melting point 168°–9° (dec.); $[\alpha]_D$ −9.3 ± 1° (c 3, 1 molar aqueous HCl).

Similar results to those of Examples 1 and 2 are obtained but in somewhat lower yield by conducting the reaction in the absence of boron trifluoride.

EXAMPLE 3

2-Fluoroputrescine from Putrescine

Putrescine (8.05 g.) was dissolved in 100 ml. of liquid hydrogen fluoride at −78° C. and boron trifluoride gas was passed in to saturation. A fluorine/helium mixture (20% F by volume) equivalent to 6 g. of fluorine was passed into the reaction mixture over a 6 hour period while being irradiated with U.V. light, stirred, and cooled in a dry ice-acetone cooling bath. The cooling bath was removed and nitrogen was bubbled through the mixture for 14 hours to remove the solvent. The residue was dissolved in concentrated hydrochloric acid, evaporated to dryness in vacuo, redissolved in 40 ml. of water, and applied to a Dowex 50 ion exchange resin column (400 ml. of resin, 30–100 mesh, H+ form). The column was washed with water, then eluted with 4 M aqueous hydrochloric acid. The fractions which gave a positive ninhydrin test were combined and evaporated to dryness to provide crude 2-fluoroputrescine dihydrochloride admixed with some starting material as the hydrochloride salt. The product was further purified by chromatography on Dowex 50×8 cation exchange resin (1.6 liters of resin in the H+ form, 200–400 mesh). The column was washed with 3 liters of water, then developed with 2.5 molar aqueous hydrochloric acid, 25 ml. fractions of eluant being collected (flow rate 750 ml. hour). The product was shown by proton NMR to be incorporated in fractions 221–280. These fractions were combined and evaporated to dryness in vacuo to give 2-fluoro-putrescine dihydrochloride, melting point 247°–249° C. (dec.). A sample (300 mg.) was recrystallized for analysis by dissolving it in 15 ml. of methanol and adding 30 ml. of isopropanol to give 200 mg. of the novel compound, 2-fluoroputrescine dihydrochloride, m.p. 251°–253° C.

EXAMPLE 4

Fluorospermine from Spermine

A solution of spermine (8.2 g.) in 100 ml. of liquid hydrogen fluoride was saturated with boron trifluoride gas at −78° C. Then under irradiation with light a fluorine/helium mixture (20% fluorine by volume) was passed into the reaction mixture over 6½ hours while being stirred and cooled in a dry ice-acetone bath. After removal of the cooling bath, the solvent was evaporated by bubbling through it a stream of nitrogen gas. The residue was dissolved in concentrated hydrochloric acid, evaporated to dryness in vacuo and subjected to a preliminary purification on a Dowex 50 resin column as described in Example 3. The crude tetrahydrochloride mixture obtained was separated on a Dowex 50×8 cation exchange resin column (1.5 liters of resin, 200–400 mesh, H+ form) by elution with water then with aqueous hydrochloric acid, 20 ml. fractions being collected; flow rate of eluant, 1200 ml./hr.

| Fractions | Fluate |
|---|---|
| 1–290 | 2.5M HCl |
| 291–530 | 3.0M HCl |
| 531–880 | 3.5M HCl |
| 881–1070 | 4.0M HCl |

Pooled fractions 811–840 were evaporated to dryness and found by proton magnetic resonance spectroscopy to contain difluoro-spermine tetrahydrochloride.

The residue on evaporation of fractions 871–930 was monofluoro-spermine tetrahydrochloride of the following structure:

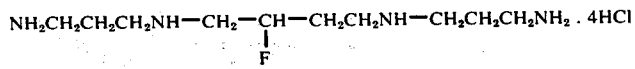

This novel product, N,N'-bis(3-aminopropyl)-1,4-diamino-2-fluorobutane tetrahydrochloride, (1 g.) was crystallized by dissolving it in 10 ml. of water and adding methanol to incipient cloudiness (40 ml.) and cooling overnight; m.p. >270° C.

EXAMPLE 5

4-Fluoro-L-Ornithine from L-Ornithine

L-ornithine hydrochloride (16.85 g.) was dissolved in 200 ml. of liquid hydrogen fluoride, and the solvent was evaporated under a stream of dry nitrogen at room temperature. The residual L-ornithine hydrochloride was redissolved in 200 ml. of liquid hydrogen fluoride and the solution was saturated with boron trifluoride gas at −78° C. A fluorine/helium mixture (20% fluorine by volume) was bubbled into the reaction mixture for 20 hours (about 460 milliatoms of fluorine) while stirring and cooling in dry ice-acetone and irradiating with U.V. light. The solvent was removed under a stream of nitrogen gas and the residue was dissolved in water and evaporated to dryness in vacuo. The residue was redissolved in water and purified on a column of IRA 120 ion exchange resin (400 ml. in the $H^+$ form) by elution with 250 ml. of water followed by 2 liters of 3 N hydrochloric acid. Evaporation of the acid effluent gave crude 4-fluoro-L-ornithine dihydrochloride. The crude product was further purified on a column of Dowex 50 cation exchange resin (1500 ml., 200–400 mesh, $H^+$ form) by elution with water, followed by 2 molar hydrochloric acid at a flow rate of 500 ml./hour, 23 ml. fractions being collected. Evaporation of fractions 351–400 gave 2 gm. of novel 4-fluoro-L-ornithine dihydrochloride, which is transformed by treatment with a stoichiometric amount of pyridine in isopropanol into 4-fluoro-L-ornithine monohydrochloride, m.p. 178°–185° C. (decomposition).

EXAMPLE 6

Photofluorination of t-butylaminoethanol

Boron trifluoride gas (10 g.) was added to a mixture of 2.47 g. of t-butylaminoethanol in 40 ml. of liquid hydrogen fluoride at −78° C. With continued cooling and stirring a fluorine/nitrogen mixture (20% fluorine by volume) (0.1 g. atoms of fluorine) was introduced to the reaction mixture over 3½ hours while being irradiated with U.V. light. The cooling bath was removed and the solvent was evaporated under a stream of dry nitrogen gas. The residue was dissolved in water, evaporated to dryness in vacuo, and redissolved in water. The solution was purified on a Dowex 50 cation exchange resin column (200 ml., $H^+$ form) by elution with 2 liters of water, followed by 4 molar hydrochloric acid. The product obtained by evaporation of eluant was 3.1 g. of a colorless solid representing a mixture of the hydrochlorides of the novel monofluoro and difluoro t-butylaminoethanol of the following structures as determined by FMR spectroscopy:

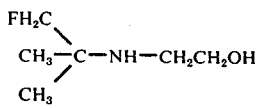

N-[(1-fluoromethyl-1-methyl)ethyl]ethanolamine

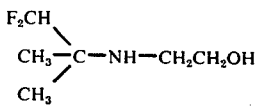

N-[(1-difluoromethyl-1-methyl)ethyl]ethanolamine

Another experiment, done under similar conditions but without irradiation with light, gave essentially unchanged starting material.

EXAMPLE 7

Fluorination of 2-aminobutyric Acid

2-Aminobutyric acid (1.03 g.) was dissolved in 50 ml. of liquid hydrogen fluoride and a mixture of fluorine/helium gases (20% fluorine by volume) was introduced over one hour (about 30 milliatoms of fluorine) under stirring and cooling in a dry ice-acetone bath. A sample of the solution was analyzed by Spinco-Beckman automatic amino acid analyzer to show the presence of 3-fluoro-2-amino-butyric acid (about 1% yield) and of 4-fluoro-2-aminobutyric acid (about 3% yield.). Into the remaining reaction mixture the fluorine/helium mixture was introduced for one hour while the temperature was maintained at 0° C. The residue obtained after evaporation of the solvent contained 3-fluoro-2-aminobutyric acid (about 8% yield) as well as 4-fluoro-2-aminobutyric acid (about 30% yield).

EXAMPLE 8

Fluorination of 2-aminobutyric Acid in Liquid Hydrogen Fluoride/Antimony Pentafluoride 2-Aminobutyric acid (1.03 g.) was dissolved in 50 ml. of liquid HF, while cooling in a dry ice-acetone bath. Antimony pentafluoride (0.9 g.) was then added and a stream of F/He passed in, employed in 2 increments. F/He, containing 30mg.-atom F was passed in under cooling with dry ice-acetone in a one-hour period, followed by the same amount of F/He mixture while under cooling in an ice-water bath (1 hour).

The HF solvent was removed by passing through a stream of nitrogen. The residue was dissolved in water and analyzed by Spinco-Beckman amino acid analyzer, to indicate 31% yield of 4-fluoro-2-aminobutyric acid, 7% yield of 3-fluoro-2-aminobutyric acid, in addition to 50% of the starting material.

EXAMPLE 9

Photofluorination of Polyacrylic Acid

A solution is prepared by dissolving 1.8 g. of polyacrylic acid in 40 ml. of liquid HF, then while irradiating with U.V. light and stirring in a dry ice-acetone cooling bath, a F/He mixture (20 v. % of F) was passed in for 1½ hours (approximately 44 milliatoms of F). The solvent was evaporated and the solid colorless mass remaining was dried in vacuo. Elementary analysis showed that the product contained 13.4% of organically bound F.

A similar experiment run in the dark gave F-free product.

EXAMPLE 10

Photofluorination of Polyvinyl Chloride

Polyvinyl chloride (10 g., about 0.16 g-mole chromatographic grade from Polysciences, Inc.) was suspended in 150 ml. of liquid HF. A stream of F/He mixture (20% F by volume) was passed in, while magnetically stirring and irradiating with U.V. light source. The temperature was kept at −78° C. by immersion of the reactor into a dry ice-acetone bath. In the 18 hours reaction period, ~19 g. of F was employed. The HF solvent was removed by evaporation aided by a stream of nitrogen gas. The powdery, colorless residue was washed free of HF by refluxing it with 100 ml. ethanol, then dried in vacuo at 64° C., to give colorless polymer containing 14.25% of F and 45.9% of Cl.

EXAMPLE 11

Fluorination of Polycaprolactam

Polycaprolactam (Zytel 211, brand of nylon), (5.0 g.; 44.5 g. millimole units) was dissolved in 70 ml. liquid hydrogen fluoride. A mixture of He/F (20 v. % F) was passed in for 3 hours under stirring and cooling in a dry ice-acetone bath (~45 mmoles of F). The solvent was removed by evaporation in a stream of $N_2$ and the residue was triturated with methanol to give a slurry of snow white particles. The pH was brought to ~8 (pyridine), then it was filtered, washed with methanol and dried in vacuo to give 4.8 g. of colorless powder of fluorinated polycaprolactam with 2.6% F-content.

A similar experiment was run with the difference that 10 g. of $BF_3$ was added before fluorination. The product contained only traces of fluorine.

What is claimed is:

1. A process for substitutive C-fluorination of an organic substrate which is D-alanine, 2-deutero-D-alanine, putrescine, spermine, t-butylamino ethanol, L-ornithine, 2-aminobutyric acid, polyacrylic acid, polyvinylchloride, or polycaprolactone comprising dissolving or suspending the substrate in liquid hydrogen fluoride, liquid hydrogen fluoride containing boron trifluoride, or liquid hydrogen fluoride containing antimony pentafluoride at −80° to 15° C. and introducing fluorine thereto under irradiation with light.

2. The process of claim 1 wherein the fluorine is introduced as a mixture with a rare gas or nitrogen.

3. A process for the preparation of a compound of formula

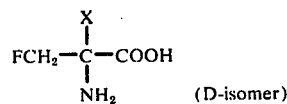

(D-isomer)

or acid addition salt thereof, wherein X is hydrogen or deuterium which comprises dissolving a compound of formula:

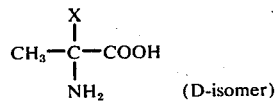

(D-isomer)

in liquid hydrogen fluoride containing boron trifluoride or liquid hydrogen fluoride containing antimony pentafluoride at −80° to 15° C. and introducing fluorine thereto under irradiation with light.

4. The process of claim 3, wherein the fluorine is introduced as a mixture with a rare gas or nitrogen.

5. The process of claim 3, wherein the solvent is liquid hydrogen fluoride containing boron trifluoride up to the saturation point.

6. The process of claim 5 wherein the fluorine is introduced as a mixture with a rare gas or nitrogen containing 1–20% by fluorine.

* * * * *